(12) United States Patent
McNeff et al.

(10) Patent No.: US 6,440,475 B1
(45) Date of Patent: Aug. 27, 2002

(54) GRAIN MOISTURE MEASURING APPARATUS AND METHOD

(75) Inventors: Larry McNeff, Hopkins; Steve Rupp, Minnetonka; Matt Wendorf, Plymouth; Joel Claflin, Coon Rapids; Clayton McNeff; Pete Greuel, both of Anoka; Lowell Sedler, Stanchfield, all of MN (US)

(73) Assignee: SarTec Corporation, Anoka, MN (US)

( * ) Notice: Subject to any disclaimer, the term of this patent is extended or adjusted under 35 U.S.C. 154(b) by 0 days.

(21) Appl. No.: 09/396,801

(22) Filed: Sep. 14, 1999

(51) Int. Cl.⁷ .......................... A23L 1/00; A23N 17/00; G01N 33/00
(52) U.S. Cl. ...................... 426/231; 73/73; 99/487; 99/536; 426/507
(58) Field of Search ................... 426/231, 507, 426/518; 99/487, 516, 536; 73/73

(56) References Cited

U.S. PATENT DOCUMENTS

| | | | |
|---|---|---|---|
| 3,714,818 A | * | 2/1973 | Relph ............................. 73/73 |
| 3,732,435 A | | 5/1973 | Strandberg, Jr. et al. |
| 3,744,144 A | | 7/1973 | Weis |
| 4,386,471 A | | 6/1983 | Bowrey et al. |
| 4,499,111 A | | 2/1985 | Oetiker et al. |
| 4,558,523 A | | 12/1985 | Isbell et al. |
| 4,630,489 A | | 12/1986 | Fisher et al. |
| 4,644,665 A | | 2/1987 | Naunapper et al. |
| 4,696,115 A | | 9/1987 | Spadafora |
| 4,748,400 A | | 5/1988 | Typpo |
| 4,898,092 A | | 2/1990 | Greer |
| 4,993,316 A | | 2/1991 | Greer |
| 4,994,286 A | | 2/1991 | Greer |
| 5,133,982 A | | 7/1992 | Bodkin et al. |
| 5,139,779 A | | 8/1992 | McNeff |
| 5,194,275 A | | 3/1993 | Greer |
| B14,898,092 A | | 10/1993 | Greer |
| 5,347,468 A | | 9/1994 | Rupp et al. |
| 5,437,882 A | * | 8/1995 | Greer et al. ................... 99/487 |
| 5,886,533 A | * | 3/1999 | Satake et al. ................ 426/231 |

OTHER PUBLICATIONS

Butcher, J., "Automatic Control of Wheat Conditioning," *Milling*, vol. 152(6) pp. 44, 46, 48, 50, 52 (1970).

(List continued on next page.)

Primary Examiner—George C. Yeung
(74) Attorney, Agent, or Firm—Merchant & Gould P.C.

(57) ABSTRACT

A grain moisture measuring apparatus and method for measuring the moisture content of the grain as the grain moves through a grain conditioning system in which moisture is applied to the grain at a first location. The grain moisture measuring apparatus includes a sample extraction mechanism located at a point downstream from the first location where moisture is applied to the grain. The sample extraction mechanism extracts a sample of grain from the grain moving through the grain conditioning system. A grinding mechanism is connected to the sample extraction mechanism with the grain sample being transferred to the grinding mechanism which then grinds the sample to physically alter the sample. The apparatus further includes a moisture sensor positioned adjacent the grinding mechanism wherein the sample of grain is transferred to a location adjacent the moisture sensor after the grain sample is ground so that the moisture sensor measures the moisture content of the grain sample. Preferably the moisture sensor is a capacitance-type sensor which provides an electronic signal that corresponds to the moisture content of the grain sample. A method is provided for measuring the moisture content of grain as the grain moves through a grain conditioning system in which moisture is applied to the grain at a first location. The method includes the steps of extracting a sample of grain from the grain moving through the grain conditioning system at a point downstream from the first location where moisture is applied to the grain; grinding the sample of grain to physically alter the sample; and measuring the moisture content of the grain sample after the grain sample has been ground.

19 Claims, 4 Drawing Sheets

OTHER PUBLICATIONS

"Cetec Tempertron," Cereal Technologies, Inc., 7 pages (Date Unknown).

"H₂O–Kay, The World's Most Advanced Grain Tempering System," *Henry Simon LTD*, Cheshire, England, 4 pages (Date Unknown).

"Wheat Tempering, Moisture Measurement and Control," published by Kay–Ray, Inc., Arlington Heights, Illinois, 5 pages (Date Unknown).

"ACCU–Sense, On–Line Non–Contacting Moisture Measurement System," published by Kay–Ray, Inc., Arlington Heights, Illinois, 7 pages (1982).

"Humidifier system for flour mills, feed mill industry, silo moisturizing," published by Agromatic AG Wald–ZH, 4 pages (Date Unknown).

"The Boonton Milltrol System," *Moisture Bulletin*, Boonton Polytechnic Company, vol. 1, No. 5, 3 pages (Aug. 1964).

Dickey–john brochures, 13 pages (Date Unknown).

"Moisture in Grain," Foss America, Inc., 5 pages (Date Unknown).

"APAC III Systems and Flour Mills," Agridustrial Electronics, Inc., Battendorf, Iowa, 13 pages (Apr. 15, 1976).

"Automatic Moisture Control—AQUATRON," Buhler–Miag, 2 pages (Date Unknown).

Brochure, "Apply liquids to dry solids 99% accurately . . . with Acecoat™ and WeighKote™", ACECO Automatic Control Electronics, 4 pages (Dec. 1983).

\* cited by examiner

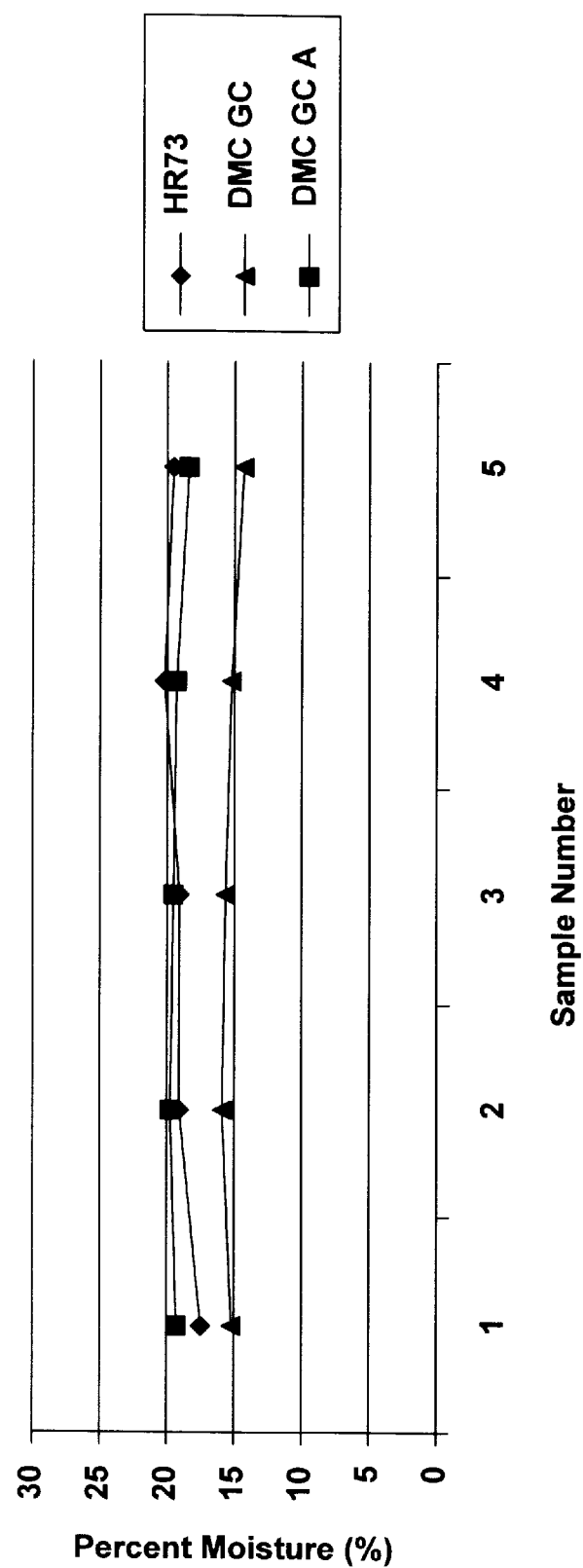

GRAIN MOISTURE MEASURING APPARATUS AND METHOD

BACKGROUND OF THE INVENTION

1. Field of the Invention

This invention relates generally to the field of grain conditioning systems and more particularly to a grain moisture measuring apparatus and method.

2. Description of the Art

Moisture control has always been a factor in milling. Grain purchased from a number of suppliers may have moisture content varying anywhere from 10 to 30 percent of its body weight. In flour milling, such variation in moisture can result in mill chokes or inferior or off-color product. In feed milling, such variation can result in waste due to brittle or improperly conditioned feed. This moisture variation can also vary the energy content of the as-fed ration, which causes variation in animal gain performance. Since the typical mill can process several hundred tons of grain every day, a mill may see fairly rapid swings over a relatively short time in the moisture level of the grain being processed.

To counteract this problem and in order to provide a mill with grain having a more uniform moisture level, grain conditioning systems have been proposed for tempering the grain before it is processed in order to increase its moisture level. A grain conditioning system adds a liquid to the grain as it is loaded into a grain elevator or as it flows into the mill. Typically, grain conditioning systems determine the amount of liquid to be added by measuring the moisture content of the dry (unconditioned) grain, the wet (conditioned) grain, or both dry and wet grain. Systems in which the amount of water added to the grain is determined by measurements of the moisture level of the dry grain are termed feedforward systems. Systems in which the amount of water added is determined not from the dry grain but from the moisture level of already conditioned grain are termed feedback systems. In practice, tempering has been shown to reduce mill stoppages and chokes due to fluctuating mill balance and improve both the efficiency of the milling process and the quality of the end product.

A feed forward system for controlling liquid added to a material such as feed grain during a conditioning process is taught generally by U.S. Pat. No. 5,194,275 to Greer. Greer discloses a feed grain delivery system in which dry grain readings are used to control the amount of moisture added to feed grain in order to raise the moisture content to a relatively constant target level. Since conditioning systems based solely on dry material readings do not measure moisture content in the conditioned product, such feed forward systems are susceptible to variations in the conditioning process due to temperature and changes in water pressure. Variations are also caused due to possible incomplete incorporation of added water into the grain (i.e., incomplete mixing of water and grain). These systems are unable to determine what, if any, effect the conditioning process is having on the material being conditioned and, therefore, cannot adapt to changing conditions.

A feed back system for controlling liquid added to grain during the conditioning process is taught generally in U.S. Pat. No. 3,732,435 to Strandberg, Jr. et al. Strandberg teaches the placement of a moisture sensor at the output of the moisture conditioner. The range at which water is added to or removed from the material is controlled by varying the speed at which the material is exposed to a constant flow of moisture or drying air. In another type of feed back system, a controller is used to adjust the amount of water added to a grain in order to bring the moisture level of the conditioned grain to approximately the target moisture level. U.S. Pat. No. 5,347,468 to Rupp et al. teaches a feed back system for controlling the addition of a liquid to a continuous flow of material and describes an algorithm for controlling the amount of water added during the hydration process.

Since, however, feed back systems do not track the moisture of incoming (dry) grain, they can be confused when wet grain moisture level readings vary due to changes in the dry grain moisture level. Additionally, the ability of feed back systems to track the target moisture level is compromised by the non-homogenized grain samples which have recently been wetted. In other words, the water on the outside and inside of the grain samples differs. The water absorbed by the grain is bound while the water remaining on the outside of the grain is unbound or "free" water. This "free" water is the root cause of erratic electrical characteristics of the grain samples in a feed back system. Furthermore, "free" water on the outside of grain "blinds" a capacitance type measurement which tends to show maxed out (invalid) readings with recently wetted samples. In general, "free" water complicates all types of moisture measurement, i.e., infra-red, microwave, or capacitance.

The erratic and unstable electrical characteristics of many materials immediately after the addition of water hinders the ability to obtain accurate, precise measurements of moisture content. Capacitance-type grain moisture measuring devices which treat a grain sample as a dielectric will not generally function properly unless the treated grain has had sufficient time to equilibrate and thus allow surface moisture to penetrate into the grain kernel. Typically, the equilibration times are on the order of hours. Such a time frame is not readily applicable to a grain processing environment where the continuous flow of grain being treated requires nearly instantaneous measurements of grain moisture levels to appropriately condition the grain as it moves through the system. If the treated grain is not allowed sufficient time to equilibrate, the erratic, unstable dielectric properties of the grain make it difficult to accurately measure the moisture level in the recently hydrated material. This instability becomes more apparent as the level of hydration increases. For these reasons, manufacturers will typically restrict a feed back system to use with products which absorb and stabilize moisture rapidly (such as soybean meal and mill feed).

It is apparent that feed back controlled grain conditioning systems, since they operate on the basis of the finished product, should be best capable of reacting to and compensating for changes in grain and water flow conditions. These systems, however, have been limited by their linability to accurately and efficiently measure the moisture level of recently wetted (unequilibrated) grain due to the unstable and erratic electrical characteristics of such materials. Additionally, the cost of such systems are typically higher than other types of systems.

There is a need for an apparatus and method for accurately measuring the moisture of grain as the grain moves through a grain conditioning system. Further, an apparatus and method is needed for accurately and efficiently measuring the moisture level of materials recently wetted to achieve a target level for moisture for the material.

SUMMARY OF THE INVENTION

The present invention provides a grain moisture measuring apparatus and method for measuring the moisture content of the grain as the grain moves through a grain conditioning system in which moisture is applied to the grain at a first location. According to one aspect of the present invention, the grain moisture measuring apparatus includes a sample extraction mechanism located at a point downstream from the first location where moisture is applied to the grain. The sample extraction mechanism extracts a sample of grain from the grain moving through the grain conditioning system. A grinding mechanism is connected to the sample extraction mechanism with the grain sample being transferred to the grinding mechanism which then grinds the sample to physically alter the sample. The apparatus further includes a moisture sensor positioned adjacent the grinding mechanism wherein the sample of grain is transferred to a location adjacent the moisture sensor after the grain sample is ground by the grinding mechanism so that the moisture sensor measures the moisture content of the grain sample. Preferably, the moisture sensor is a capacitance-type sensor which provides an electronic signal that corresponds to the moisture content of the grain sample. However, the moisture sensor may be any device that measures grain moisture including but not limited to microwave, infrared. capacitance, chemical, or gravimetric sensors.

According to another aspect of the present invention, a method is provided for measuring the moisture content of grain as the grain moves through a grain conditioning system in which moisture is applied to the grain at a first location. The method includes the step of extracting a sample of grain from the grain moving through the grain conditioning system at a point downstream from the first location where moisture is applied to the grain. Further steps include grinding the sample of grain to physically alter the sample and measuring the moisture content of the grain sample after the grain sample has been ground.

Pursuant to another aspect of the present invention, a grain conditioning system for conditioning a continuous flow of grain to a target moisture level is provided which incorporates the moisture measuring apparatus of the present invention. Such an apparatus includes a fluid control valve connected to a sprinkler head where the fluid control valve is capable of being set to a desired liquid flow rate in order to control the flow of a liquid to the sprinkler head. The apparatus further includes an auger positioned to convey grain past the sprinkler head in order to condition the grain. A sample extraction mechanism is located at a point downstream from the sprinkler head so that the sample extraction mechanism exacts a sample of grain from the grain moving through the auger. A grinding mechanism is connected to the sample extraction mechanism such that the sample of grain extracted from the sample extraction mechanism is transferred to the grinding mechanism and the grinding mechanism grinds the grain sample to physically alter the grain sample. A moisture sensor is positioned adjacent to the grinding mechanism with the sample of grain being transferred to a location adjacent the moisture sensor after the grain sample is ground by the grinding mechanism such that the moisture sensor measures the moisture content of the grain sample and provides a first electronic signal that corresponds to the moisture content of the grain sample. The apparatus further includes a processor connected to the fluid control valve and the moisture sensor wherein the processor receives the first electronic signal from the moisture sensor that corresponds to the moisture content of the grain sample and the processor creates an output control signal which controls the operation of the fluid control valve so that the fluid control valve permits a desired liquid flow rate that corresponds to the output control signal from the processor so that the moisture level of the conditioned grain approximates the target moisture level.

BRIEF DESCRIPTION OF THE DRAWINGS

FIG. 4 is a graph of experimental data derived from testing of the moisture measuring apparatus.

DETAILED DESCRIPTION OF THE INVENTION

Figure 1:
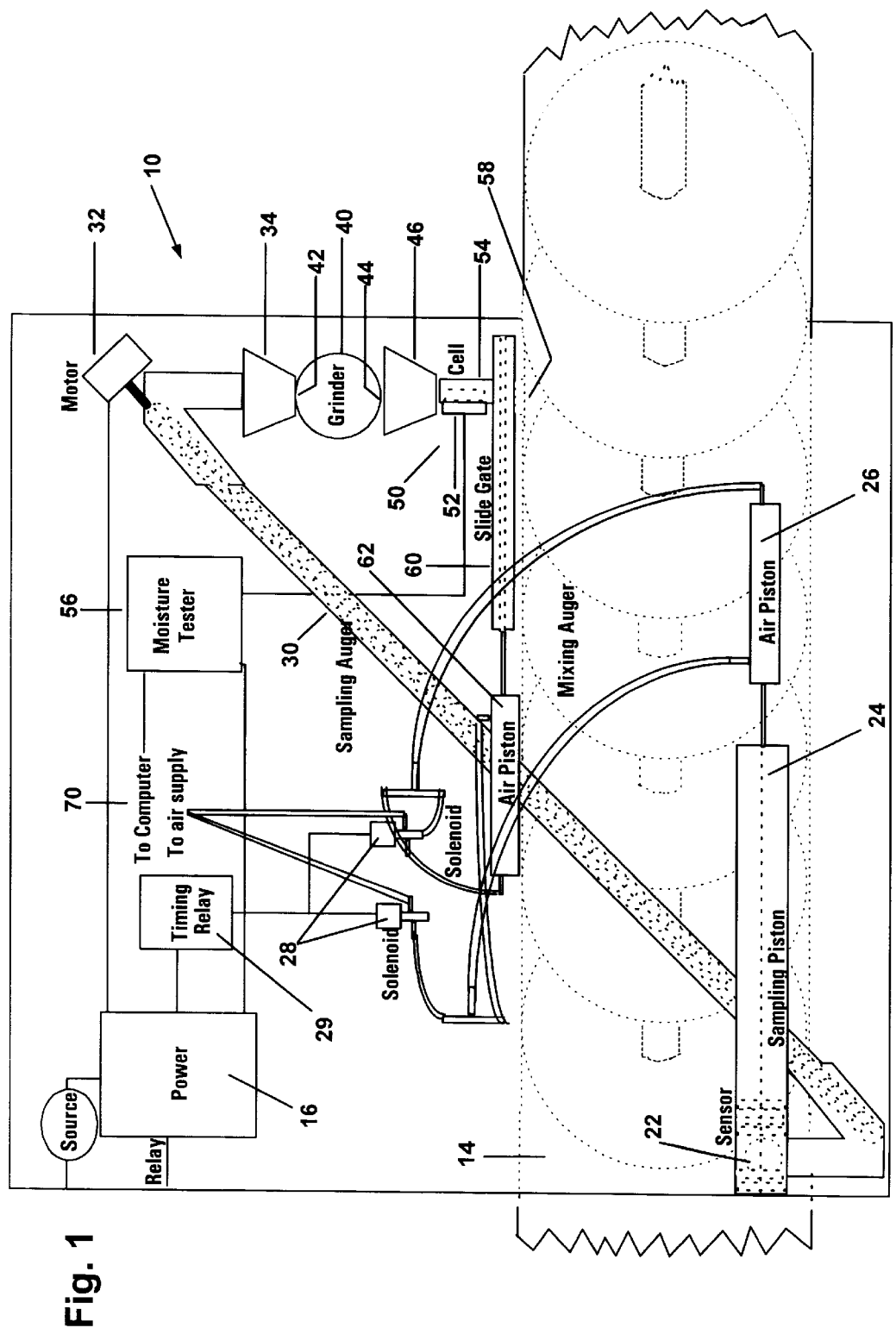
FIG. 1 is a side plan view of one embodiment of a moisture measuring apparatus according to the principles of the present invention.

Referring now to the drawings in which similar elements are numbered identically throughout, a description of the preferred embodiments is provided. In FIG. 1, a side plan view of a grain moisture measuring apparatus according to the principles of the present invention is generally illustrated at 10. The grain moisture measuring apparatus 10 is preferably adapted for use in a grain conditioning system such as found in a typical feed mill where the grain is conditioned by adding moisture to achieve a target moisture level. Referring to FIG. 1, the moisture measuring apparatus 10 includes a sampling mechanism 20 for extracting a sample of the grain from the grain conditioning system. In the illustrated embodiment shown in FIG. 1, the grain is moving through the mixing auger 14 with the grain already having had liquid applied to it at a point upstream from the sampling mechanism 20. The sampling mechanism 20 includes an aperture 22 in connection with the mixing auger 14 such that grain may flow from the mixing auger through the aperture 22 for collection of a grain sample whose moisture is measured.

In a preferred embodiment, the sampling mechanism 20 is designed to automatically and periodically extract a predetermined sample of grain from the mixing auger 14 to determine the moisture content of the sample. In a preferred embodiment, the sampling mechanism includes a sampling piston 24 connected to an air piston 26 which is connected to a corresponding air supply. Solenoid valves 28 or other similar control mechanisms are utilized in conjunction with a timing relay or controller 29 so that the solenoids periodically activate the air piston to drive the sampling piston. In this way, a predetermined amount of grain is permitted to exit through the aperture 22 to constitute a sample for testing. After the sample has been collected, the solenoid 28 activates the air piston 26 to block access to the aperture 22 from the mixing auger 14.

In one preferred embodiment, a sampling auger 30 is provided to transport the sample of grain removed from the mixing auger 14 to a location above the mixing auger for subsequent moisture testing. The sampling auger 30 is driven by a corresponding motor 32 and transports the grain sample to a location above the mixing auger 14 and then deposits the grain sample into a funnel or other similar structure for directing the grain sample into the grinding mechanism or grinder 40. The sampling auger 30 as well as the solenoids 28 are driven by a power source 16.

The grinder receives the freshly wetted sample of grain and grinds the sample to physically alter the grain sample. In one embodiment, the grinder used in the moisture sensing apparatus is a model 4-E Quaker City Mill (Philadelphia, Pa.). It is appreciated that by grinding the grain sample to physically alter the freshly wetted grain sample, the grinder allows the grain sample to more quickly absorb the liquid applied to it by increasing the surface area of the grain sample. After grinding, the ground grain sample is transferred to the moisture sensor 50 to determine the moisture content of the grain sample. In one embodiment, the grinder 40 is positioned above the moisture sensor 50 so that after grinding, the grain sample is permitted to flow, under the influence of gravity, to the moisture sensor 50. Preferably, the moisture sensor 50 includes a cell 52 which is disposed within a chamber or housing such as a cylindrical structure 54 for receiving the grain sample. In one embodiment, a funnel 46 is provided to direct the ground grain exiting from the grinder 40 to the moisture sensor 50. The cell 52 of the moisture sensor 50 then measures the moisture content of the ground grain sample to determine the moisture content of the grain sample. In one embodiment, moisture sensor 50 constitutes a capacitance type moisture sensor for measuring the moisture content of the ground grain sample. One such typical capacitance type moisture sensor for use in the present invention is the Calcu-Dri Moisture Monitor model 602N213 manufactured by David Manufacturing Co. (DMC). The moisture sensor 50 preferably generates an electronic signal which corresponds to the moisture content of the grain sample. In one embodiment, the cell 52 measures the moisture content of the sample and provides an electronic signal to the moisture tester 56 which then converts the signal from the cell 52 to an electronic signal corresponding to the moisture content of the sample. This electronic signal may then be translated into a visual readout to indicate the moisture content of the sample being tested. Further, the electronic signal may be provided to a processor or computer 70 which receives the electronic signal corresponding to the moisture content of the grain sample. The processor 70 preferably controls the application of liquid to the incoming grain based on the signal received from the moisture sensor 50 so that the moisture content of the conditioned grain approximates a chosen or target moisture level. It is appreciated that various other types of moisture sensors other than a capacitance type sensor may be utilized in conjunction with the present invention, including but not limited to microwave, infrared, chemical, or gravimetric sensors.

Referring to FIG. 1, the moisture sensor 50 may preferably include a mechanism for retaining the grain sample adjacent the moisture sensor cell 52 and subsequently permitting the transfer of the grain back to the mixing auger 14 after the moisture level of the grain sample has been measured. In one such system, a slide gate 60 is provided in connection to an air piston 62 which is similarly connected to an air supply and a corresponding solenoid valve 28 and timing relay for control of the air piston. This slide gate 60 is preferably positioned at the bottom of the moisture sensor cylinder 54 and is movable between an open and closed position. In the closed position, the slide gate 60 prevents grain from flowing through the cylinder back into the mixing auger 14. In this way, when the grain sample is transferred from the grinder 40 to the moisture sensor 50, the slide gate 60 retains the grain sample within the cylinder 54 so that the moisture sensor cell 52 can measure the moisture content of the grain sample. After the grain sample has been measured by the moisture sensor 50, the solenoids 28 activate the air piston 62 to move the slide gate 60 to the open position such that the grain sample contained within the moisture sensor cylinder 54 is now free to fall back into the mixing auger 14. In this way, the grain sample is returned to the mixing auger 14 for further processing and does not result in any wasted grain due to the moisture measuring apparatus.

In operation, the moisture measuring apparatus is utilized as part of a method for measuring the moisture content of grain as the grain moves through a grain conditioning system. The method comprises the steps of extracting a sample of grain from the grain moving through the grain conditioning system at a point downstream from a first location where moisture is applied to the grain. The sample of grain is then ground in a grinder to physically alter or homogenize the sample of grain and the resulting ground grain sample moisture content is measured. It is appreciated that such a method allows for accurate and efficient determination of the moisture content of newly wetted ground grain in a grain conditioning system.

Figure 3:
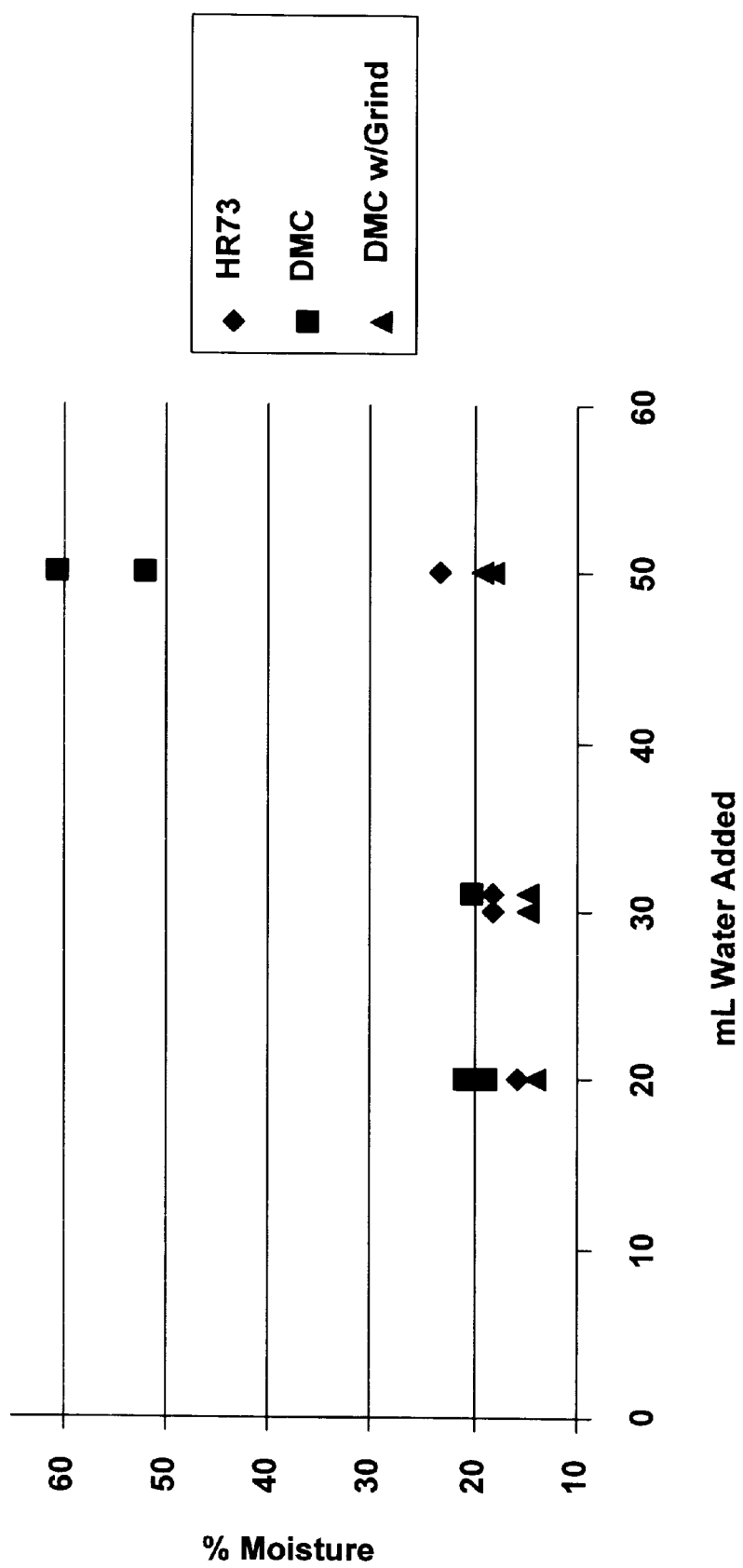
FIG. 3 is a graph of experimental data representative of percent moisture as a function of water added.

It is appreciated that the grinding of the grain sample increases the surface area of the grain to greatly enhance the absorption rate of the liquid by the grain. Preferably, the grinder grinds the grain such that the grain and liquid are substantially homogenized. By physically altering the grain sample, the liquid applied to the grain is better absorbed by the grain sample so that the moisture content measurement is much more accurate. For example, FIG. 3 is illustrative of data obtained in tests utilizing the moisture measuring apparatus 10. The data points identified as HR73 correspond to an analytical balance moisture sensor (Mettler Toledo Halogen Moisture Analyzer) which is one method of measuring the moisture content of a grain sample. The analytical balance operates on the thermogravimetric principle by first determining the weight of a sample, then heating the sample to vaporize the moisture in the sample and then weighing the dried sample to determine the moisture content. While the analytical balance provides an accurate determination of the moisture content of wetted grain, it does now allow for periodic sampling during ongoing grain processing as each sample must be heated until dry to determine its moisture content. The data points from the analytical balance (HR73) simply provide an accurate point of reference to compare with other types of moisture measuring devices. The data points corresponding to DMC represent attempts to measure the moisture content of grain through a capacitance type moisture sensor where the grain sample has not been ground after having been wetted. As illustrated in the graph in FIG. 3, as the amount of water added to the grain sample is increased, the percent moisture reading from the capacitance type moisture sensor (DMC) spikes upward (maxes out) and does not provide an accurate reading of the moisture content of the grain. This is due to the non-uniform dielectric properties of the newly wetted grain sample (i.e., non-homogenized sample) immediately after the addition of water and illustrates the problem with prior feedback moisture sensing systems. Referring to FIG. 3, the data points under the DMC w/grind represents measurements taken from the moisture measuring apparatus 10 of the present invention. As is shown in FIG. 3, grinding the grain sample after liquid has been added to the grain and then measuring the moisture content of the grain allows for much more accurate measurements of the moisture content of the grain sample. As shown in FIG. 3, the data points corresponding to the moisture measuring apparatus 10 of the present invention (DMC w/grind) correspond very closely to the data points taken by the analytical balance (HR73).

Referring to FIG. 4, the moisture measuring apparatus of the present invention may be utilized with an offset to more closely approximate the moisture content determined by other methods such as an analytical balance. For example, FIG. 4 is a graph which shows the percent moisture of five separate samples taken both by the moisture measuring apparatus of the present invention (DMC GC) and also by an analytical balance (HR73). As the graph illustrates, the moisture content measured by the moisture measuring apparatus 10 was lower than that determined by the analytical balance (HR73). Accordingly, an offset may be provided to the results yielded by the moisture measuring apparatus 10 so that the moisture content more closely corresponds to the moisture content measured by the analytical balance. For example, in FIG. 4, an offset of four moisture percentage points (4.0) was added to the moisture content determined by the moisture measuring apparatus 10 of the present invention so that a new offset moisture value (DMC GC A) is provided which more closely corresponds to the moisture content determined by the analytical balance. In this way, the determination of the moisture content of newly wetted grain is accurately and efficiently measured by the moisture measuring apparatus 10 of the present invention with the data closely corresponding to the moisture content determined by other accurate methods as well, such as an analytical balance or standard oven-dry methods.

Accordingly, the moisture measuring apparatus 10 of the present invention provides for accurate measurement of the moisture content of freshly wetted grain as part of a feedback moisture sensor and thus represents a significant improvement over the nonlinear, "blinded" results of prior feedback systems.

Referring to FIG. 1, the moisture measuring apparatus 10 is preferably adapted for automatically measuring the moisture content of a sample of grain at periodic intervals. For example, the timing relay 29 may be set up such that the solenoids 28 activate the air pistons 26, 62 for the sampling mechanism 20 and the moisture sensor 50. In one such preferred system, a sample of grain is periodically extracted from the mixing auger 14, transported to the grinder 40, where it is subsequently ground and transported to the moisture sensor cylinder 54 to measure the moisture content of the grain sample wherein the slide gate 60 then moves to the open position to permit transfer of the grain sample back to the mixing auger 14 through an appropriate aperture 58 in the mixing auger. In this way, the moisture measuring apparatus 10 automatically provides measurement of periodic samples of the freshly wetted grain sample flowing through the grain conditioning system.

It is appreciated that the moisture measuring apparatus 10 and method described above may be modified based on the particular application of the feed mill. A variety of methods may be used to extract the sample of grains either from the mixing auger or at a different location within the grain conditioning system. Additionally, it is not necessary that the sampling piston 24 and air piston 26 be used for extraction of the grain sample. Rather, the present invention simply contemplates extracting a sample of freshly wetted grain, grinding the grain sample to physically alter the sample and then measuring the moisture content of the ground sample. Within the context of this system, a variety of additional structures or mechanisms may be provided such as outlined above to assist in periodically sampling the recently wetted grain to measure its moisture content. It is not necessary, for example, to use the sampling auger to transport the grain to a position above the mixing auger. Rather, the grain could simply be permitted to fall through an aperture in the mixing auger into the grinder and then to be transported adjacent a moisture sensor for measurement after which time the grain sample may then be transferred to an appropriate container for storage or may be transferred back into the grain flowing through the grain conditioning system. Such alternative methods may be used in conjunction with the principles of the present invention. Furthermore, any moisture measuring device that is able to provide a measurement of the artificially homogenized sample within a measurement period may be used.

Figure 2:
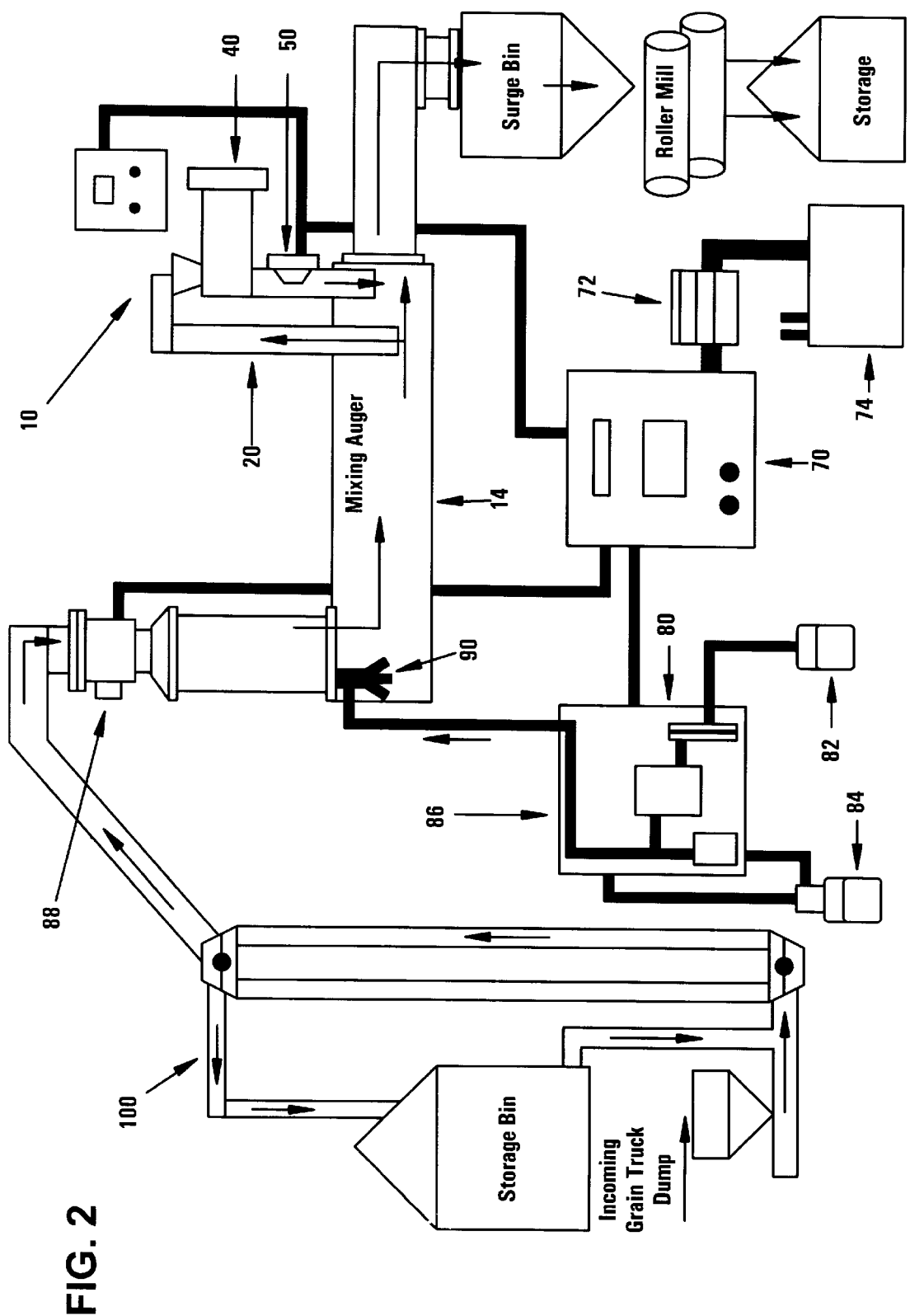
FIG. 2 is a system level block diagram representative of a grain conditioning system according to the principles of the present invention.

In a preferred embodiment, the moisture measuring apparatus 10 is used as part of a grain conditioning system to permit conditioning of the grain to a target moisture level. Referring to FIG. 2, a typical grain conditioning system consists of transporting grain from a storage bin through a mixing auger where a liquid source is added to the grain to condition the grain with the grain then continuing on for further processing such as being transported to a roller mill. A system level block diagram representative of a grain conditioning system 100 is shown generally in FIG. 2. The system I100 is a feedback system in which a processor 70 controls the application of water from a water source 82 to grain being carried on a material conveying means as mixing auger 14. A processor 70 includes a user interface so that a target moisture level can be selected for the incoming grain. The grain conditioning system I100 further preferably includes a grain flow meter 88, a flow control valve 80 and a moisture measuring apparatus 10. In the grain conditioning system 100, the grain flow meter 88 measures the flow of incoming grain while the moisture measuring apparatus 10 measures the moisture level of the conditioned or wetted grain. The processor or controller 70 increases or decreases water going through the fluid control valve 80 and responds to the grain flow and moisture level measurements. Water flows from water source 82 through flow control valve 80 to a water distributing system 90, such as a sprinkler head.

In one embodiment, the mixing auger 14 of the grain conditioning system 100 carries the grain past the sprinkler head 90 which applies water to the incoming grain. The moisture measuring apparatus 10 is located downstream from the sprinkler head and extracts a sample of the wet grain for grinding and subsequent moisture measurement by the moisture sensor 50. The moisture measurement apparatus 10 provides an electronic signal to the processor 70 corresponding to the moisture content of the conditioned or recently wetted grain, wherein the processor 70 provides a corresponding control signal to the flow control valve 80 so that the fluid control valve permits a desired liquid flow so that the moisture level of the conditioned or wetted grain approximates the selected target moisture level.

Further referring to FIG. 2, in one embodiment, the grain conditioning system 100 also includes a mixing valve 86 which operates under the control of the processor 70 to regulate the mixing of an additive to the water coming from the water supply 82. In the preferred embodiment, the chemical pump (not shown) is used to meter a constant amount of additive from an additive source 84 to the mixing valve 86. In a preferred embodiment, the additive may be a sarsasaponin-based liquid. Such liquids are used to reduce the surface tension of the water on the grain kernel, permitting easier penetration of the kernel and, therefore, faster absorption. The sarsasaponin-based additive also provides some nutrient benefits for ruminants. A method of tempering feed grain by applying to the grain a conditioning composition such as a sarsasaponin is disclosed in commonly owned U.S. Pat. Nos. 5,139,779; 5,279,838; and 5,240,727 to McNeff the entire disclosures of which are incorporated herein by reference. One such sarsasaponin-based additive designed for use in a grain conditioning system is SarTemp® which is manufactured and sold by SarTec Corporation (Anoka, Minn.).

In a preferred embodiment, the grain conditioning system 100 can be accessed by a remote or host computer 74. In the embodiment shown in FIG. 2, the system 100 further comprises communication means such as a modem 72, which operates under the control of the processor 70 to communicate over a communications medium such as a common telecommunications line to a host computer 74 or via the Internet. Addition of the modem 72 to either of the systems of FIG. 1 or FIG. 4 provides many advantages. First, technicians can access any one grain conditioning system 100 by normal telecommunications lines or via the Internet. This provides an instantaneous on-line evaluation and computer diagnostic services. For instance, preliminary diagnostic tests can be run by trained technicians operating from a remote location in order to diagnose hardware and software problems without the expense and inconvenience of an on-site diagnostic visit. Thus, hardware problems can then be resolved with a single maintenance trip. Likewise, software malfunctions can be diagnosed and programming modifications made without the need for an on-site trip. Further, software revisions can be made without extensive down time and site visits. Further, remote access can be used to accommodate electronic data transfer. For instance, the amount of sarsasaponin-based additive used can be measured by a transducer that is further monitored by software operating in the remote computer 74. System maintenance personnel can use the information gleaned from these product consumption figures to project future use of a product. These projections can then be used to schedule manufacturing of a product and to set appropriate delivery dates, which, reduces the amount of product that must be kept on hand by the customer.

It is to be understood that even though numerous characteristics and advantages of various embodiments of the present invention have been set forth in the foregoing description, together with the details of the structure and function of various embodiments of the invention, this disclosure is illustrative only and changes may be made in the details, especially in matters of shape, size, and arrangement in part within the principles of the present invention, to the full extent indicated by the broad general meaning of the terms in which the appended claims are expressed. All alternative modifications and variations of the present invention which fall within the spirit and broad scope of the appended claims are covered.

What is claimed is:

1. A grain moisture measuring apparatus for measuring the moisture content of grain as the grain moves through a grain conditioning system is which moisture is applied to the grain at a first location, the grain moisture measuring apparatus comprising:

a sample extraction mechanism located at a point downstream from the first location where moisture is applied to the grain, wherein the sample extraction mechanism extracts a sample of grain from the grain moving through the grain conditioning system;

a grinding mechanism connected to the sample extraction mechanism wherein the sample of grain extracted from the sample extraction mechanism is transferred to the grinding mechanism and the grinding mechanism grinds the grain sample to physically alter the grain sample;

a moisture sensor positioned adjacent the grinding mechanism, wherein the sample of grain is transferred to a location adjacent the moisture sensor after the grain sample is ground by the grinding mechanism such that the moisture sensor measures the moisture content of the grain sample.

2. The apparatus of claim 1 wherein the sample extraction mechanism includes a sampling piston and a timing controller such that the timing controller actuates the sampling piston to periodically permit a sample of grain to be taken from the grain moving through the grain conditioning system and delivered into the grinding mechanism.

3. The apparatus of claim 1 further comprising a housing which includes a slide gate movable between a closed and open position with the moisture sensor disposed within the housing at a location above the slide gate, wherein the slide gate is in the closed position as the sample of grain exits the grinding mechanism and flows into the housing such that the grain sample is retained within the housing and the moisture sensor measures the moisture content of the grain sample and wherein after the moisture sensor measures the moisture content of the grain sample, the slide gate subsequently moves to the open position to allow the grain sample to exit from the housing.

4. The apparatus of claim 3 further comprising a timing controller for actuating the slide gate of the housing between the closed and open position.

5. The apparatus of claim 1 wherein the moisture sensor provides an electronic signal that corresponds to the moisture content of the grain sample.

6. The apparatus of claim 1 wherein the moisture sensor is a capacitance type sensor.

7. A method for measuring the moisture content of grain as the grain moves through a grain conditioning system in which moisture is applied to the grain at a first location, the method comprising the steps of:

extracting a sample of grain from the grain moving through the grain conditioning system at a point downstream from the first location where moisture is applied to the grain;

grinding the sample of grain to physically alter the sample of grain; and measuring the moisture content of the grain sample after the grain sample has been ground.

8. The method of claim 7 wherein the step of extracting a sample of grain includes periodically actuating a sampling piston controlled by a timer controller to permit a sample of grain to be taken from the grain moving through the grain conditioning system for grinding.

9. The method of claim 8 wherein the step of measuring the moisture content of the grain sample includes providing a housing having a moisture sensor disposed therein so that the grain sample enters the housing after grinding and is contained within the housing while the moisture sensor measures the moisture content of the grain sample.

10. The method of claim 9 wherein the step of measuring the moisture content of the grain sample further includes providing a movable slide gate within the housing where the slide gate is in the closed position as grain enters the housing after being ground to retain the sample grain in the housing as the moisture sensor measures the moisture content of the grain and the slide gate subsequently moves to the open position after the moisture sensor has measured the moisture content of the grain sample so that the grain sample exits the housing.

11. A grain conditioning system for conditioning a continuous flow of grain to a target moisture level, comprising:

a sprinkler head;

a fluid control valve connected to the sprinkler head, wherein the fluid control valve is capable of being set to a desired liquid flow rate in order to control the flow of a liquid to the sprinkler head;

an auger positioned to convey grain passed the sprinkler head in order to condition the grain;

a sample extraction mechanism located at a point downstream from the sprinkler head wherein the sample extraction mechanism exacts a sample of grain from the grain moving through the auger;

a grinding mechanism connected to the sample extraction mechanism wherein the sample of grain extracted from the sample extraction mechanism is transferred to the grinding mechanism and the grinding mechanism grinds the grain sample to physically alter the grain sample;

a moisture sensor positioned adjacent to the grinding mechanism, wherein the sample of grain is transferred to a location adjacent the moisture sensor after the grain sample is ground by the grinding mechanism such that the moisture sensor measures the moisture content of the grain sample and provides a first electronic signal that corresponds to the moisture content of the grain sample; and a processor connected to the fluid control valve and the moisture sensor wherein the processor receives the first electronic signal from the moisture sensor that corresponds to the moisture content of the grain sample and the processor creates an output control signal which controls the operation of the fluid control valve so that the fluid control valve permits a desired liquid flow rate that corresponds to the output control signal from the processor so that the moisture level of the conditioned grain approximates the target moisture level.

12. The grain conditioning system of claim 11 further comprising a grain flow meter for indicating the flow of grain.

13. The grain conditioning system of claim 11 wherein the processor includes communication means for communicating with a remote computer.

14. The grain conditioning system of claim 13 wherein the communication means includes a modem.

15. The grain conditioning system of claim 11 wherein the processor includes communication means for connection to the Internet.

16. The grain conditioning system of claim 11 wherein the processor includes a user interface which can be used to select the target moisture level.

17. The grain conditioning system of claim 11 further comprising a timer controller connected to the sample extraction mechanism wherein the timer controller actuates the sample extraction mechanism to periodically permit a sample of grain to be removed from the flow of grain and transferred to the grinding mechanism.

18. The grain conditioning system of claim 11 further comprising a mixing valve in connection with a source of an additive for mixing the additive with the liquid prior to application of the liquid to the grain.

19. A method for controlling addition of liquid to a continuous flow of grain material in order to condition the grain material to a target moisture level, the method comprising the steps of:

providing a sprinkler head connected to a fluid control valve wherein the fluid control valve is capable of being set to a desired flow rate in order to control flow of liquid to the sprinkler head;

selecting a target moisture level for the grain material;

conveying the grain material past the sprinkler head in order to condition the grain material;

extracting a sample of the grain material at a point downstream from the sprinkler head;

grinding the sample of grain material to physically alter the grain material;

measuring the moisture content of the grain material after the grain material has been ground and providing a first electronic signal that corresponds to the moisture content of the grain material; and providing a processor for receiving the first electronic signal that corresponds to the moisture content of the grain material wherein the processor creates an output control signal which controls the operation of the fluid control valve so that the fluid control valve permits a desired liquid flow rate that corresponds to the output control signal from the processor so that the moisture level of a conditioned grain approximates the target moisture level.

* * * * *